United States Patent [19]
Lin

[11] Patent Number: 6,080,158
[45] Date of Patent: Jun. 27, 2000

[54] INTERVERTEBRAL FUSION DEVICE

[76] Inventor: Chih-I Lin, 14292 Spring Vista La., Chino Hills, Calif. 91709

[21] Appl. No.: 09/379,491

[22] Filed: Aug. 23, 1999

[51] Int. Cl.⁷ .................................................... A61B 17/56
[52] U.S. Cl. .......................................... 606/61; 623/17.16
[58] Field of Search ................................. 606/61, 62, 78; 623/17

[56] References Cited

U.S. PATENT DOCUMENTS

| | | | |
|---|---|---|---|
| 4,349,921 | 9/1982 | Kuntz | 623/17 |
| 5,320,644 | 6/1994 | Baumgartner | 623/17 |
| 5,423,817 | 6/1995 | Lin | 623/17 |
| 5,425,772 | 6/1995 | Brantigan | 623/17 |
| 5,443,514 | 8/1995 | Steffee | 623/17 |
| 5,607,424 | 3/1997 | Tropiano | 606/61 |
| 5,653,761 | 8/1997 | Pisharodi | 623/17 |
| 5,653,762 | 8/1997 | Pishadori | 623/17 |
| 5,766,252 | 9/1998 | Henry et al. | 623/17 |
| 5,888,224 | 3/1999 | Beckers et al. | 623/17 |
| 5,888,227 | 3/1999 | Cottle | 623/17 |

*Primary Examiner*—Jeffrey A. Smith
*Assistant Examiner*—Eduarto C. Robert
*Attorney, Agent, or Firm*—Bacon & Thomas, PLLC

[57] ABSTRACT

An intervertebral fusion device is formed of an elastic block body which is provided in the upper contact surface thereof with a plurality of downward elastic slots substantially parallel to one another, and in the lower contact surface thereof with one or more upward elastic slots substantially parallel to the downward elastic slots. The upward elastic slots and the downward elastic slots are arranged in an alternating manner. The elastic block body has a left surface and a right surface, which are substantially planar in construction. The upper contact surface and the lower contact surface of the elastic block body are of a convex construction.

8 Claims, 6 Drawing Sheets

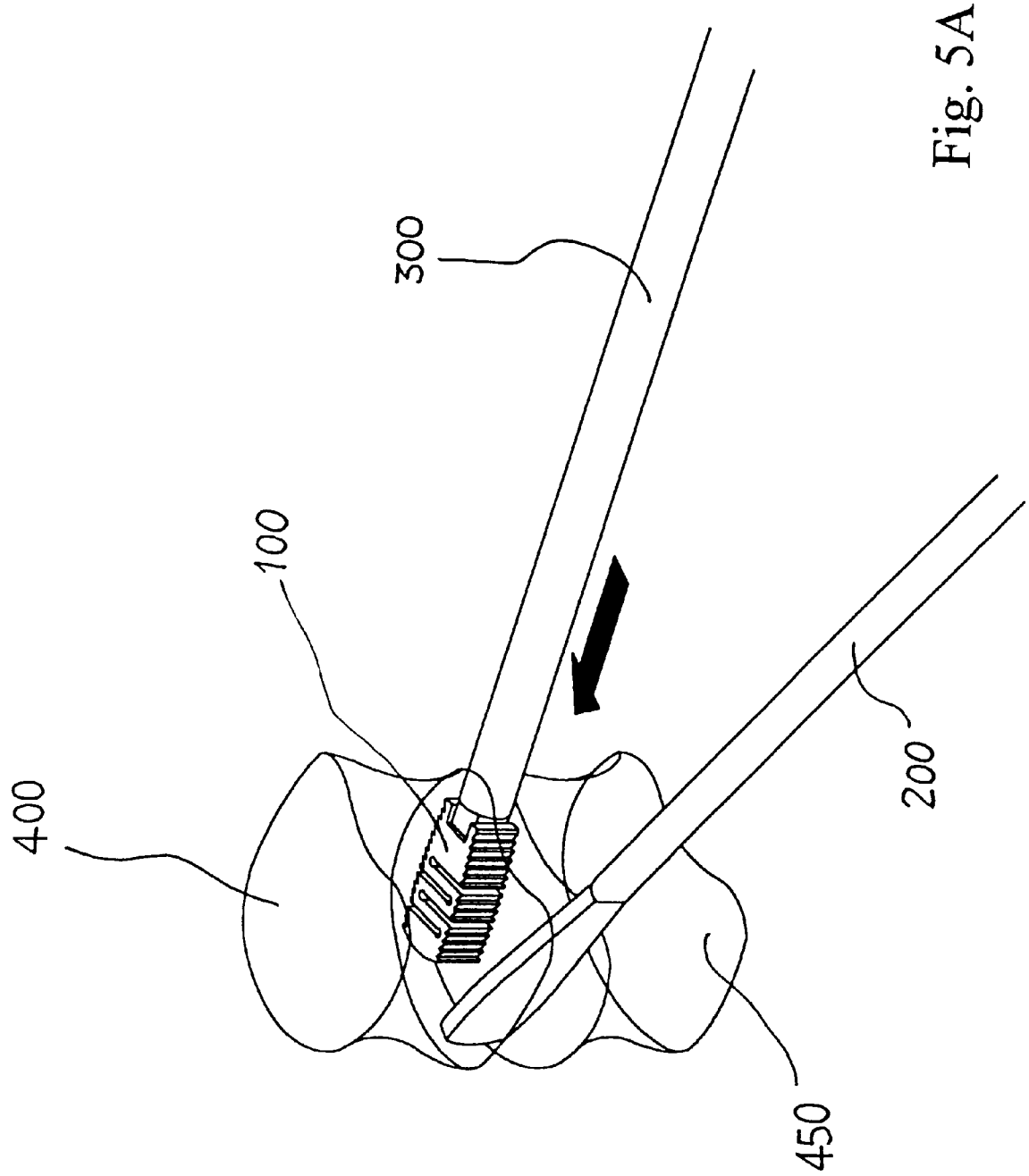

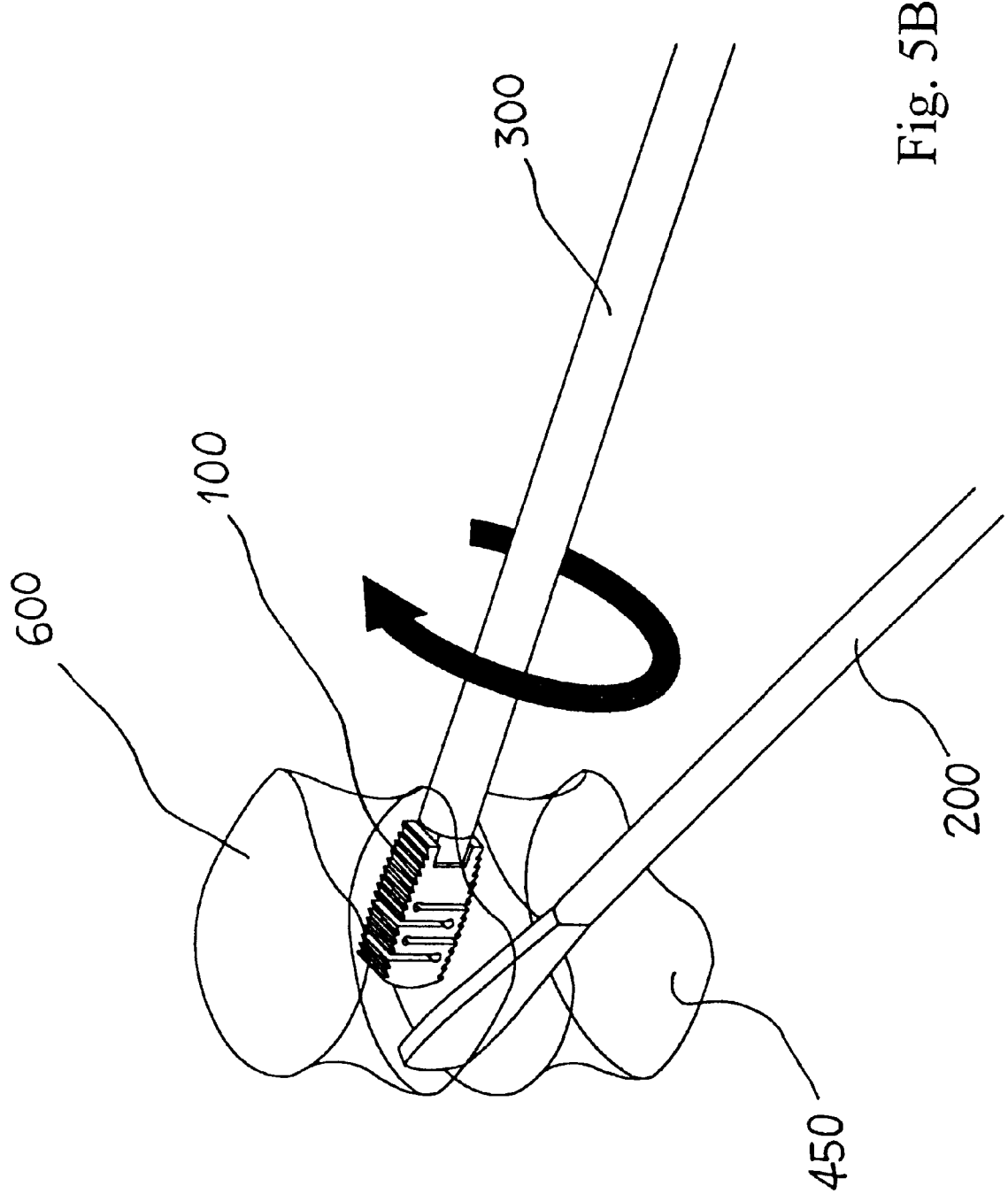

INTERVERTEBRAL FUSION DEVICE

FIELD OF THE INVENTION

The present invention relates generally to an intervertebral fusion device, and more particularly to an intervertebral fusion device capable of deforming slightly in response to the state of a force exerting on the device.

BACKGROUND OF THE INVENTION

The typical conventional intervertebral fusion device is formed of a hollow cylindrical body having a perforated periphery, and bone graft, as exemplified by the device disclosed in the U.S. Pat. No. 4,501,269, and the BAKTEM interbody fusion system disclosed in the U.S. Pat. No. 5,015,247. The interbody fusion system comprises a rigid hollow cylindrical body containing bone graft. The rigid cylindrical body can not be adjusted in relation to the relative position of vertebrae so as to suit the intervertebral space. With a view to overcoming such a drawback as described above, this inventor of the present invention discloses an adjustable intervertebral fusion device in the U.S. Pat. No. 5,423,817. The adjustable intervertebral, fusion device is found to be defective in design in that it is rather time-consuming to implant the device, and that a relatively large incision must be made to facilitate the implanting of the device, thereby resulting in the prolongation of the post-operation healing process of the patient.

SUMMARY OF THE INVENTION

It is therefore the primary objective of the present invention to provide an intervertebral fusion device with a plurality of elastic slots enabling the device to be self-adjustable, i.e. silghtly elastic, after intervertebral implantation.

It is another objective of the present invention to provide an intervertebral fusion device which is provided on the upper and the lower contact surfaces thereof with a projection to facilitate the fastening of the device with the vertebrae.

It is still another objective of the present invention to provide an intervertebral fusion device which has a left surface, a right surface, in addition to the upper contact surface and the lower contact surface. The distance between the left surface and the right surface is smaller than the distance between the upper contact surface and the lower contact surface. As a result, the device of the present invention simplifies the surgical operation, as shown in FIGS. 5A to 5C.

It is still another objective of the present invention to provide an intervertebral fusion device with an upper contact surface and a lower contact surface, which are substantially arcuate in construction, and with a left contact surface and a right contact surface, which are substantially parallel to each other.

The device of the present invention has a plurality of sides, which are designated as upper, lower, front, rear, left, and right. Such designations are consistent with upper, lower, front, rear, left, and right sides of the human body in a standing position.

The intervertebral fusion device of the present invention is formed of an elastic block body having a substantially rectangular shape, with is provided in the upper contact surface thereof with a plurality of downward elastic slots substantially parallel to one another, and in the lower contact surface thereof with one or more upward slots substantially parallel to the downward elastic slots. The downward elastic slots and the upward elastic slots are arranged in an alternating manner. The elastic block body has a left surface and a right surface, which are substantially planar in construction. The upper contact surface and the lower contact surface of the elastic block body are of a convex construction.

The elastic block body is made of any biologically compatible material, such as a stainless steel 316LVM, Ti-6-4, cobalt-molybdenum-nickel alloy, etc.

Preferably, the left surface and the right surface of the elastic block body are substantially planar in construction. More preferably, the left surface and the right surface are substantially parallel to each other.

The upper contact surface and the lower contact surface of the elastic block body are substantially convex in form. These two convex surfaces are provided with a plurality of protrusions which are either regular or irregular in form. The protrusions may be arranged in a serrated or stripe manner.

The upper contact surface has one or more downward elastic slots, preferably two to five in number.

The lower contact surface has one or more upward elastic slots, preferably two to five in number.

Preferably, the upward elastic slot and the downward elastic slot are substantially parallel to each other. When the elastic block body is provided with a plurality of upward elastic slots and downward elastic slots, these slots are preferably arranged in an alternating manner, such as "downward upward downward upward downward upward," "downward downward upward downward upward upward," "downward upward upward downward downward upward," etc.

The foregoing objectives, features, functions, and advantages of the present invention will be more readily understood upon a thoughtful deliberation of the following detailed description of the embodiments of the present invention with reference to the accompanying drawings.

BRIEF DESCRIPTION OF THE DRAWINGS

FIGS. 5A–5C are schematic views of a surgical operation to implant a device of a second preferred embodiment of the present invention.

DETAILED DESCRIPTION OF THE EMBODIMENTS

Figure 1:
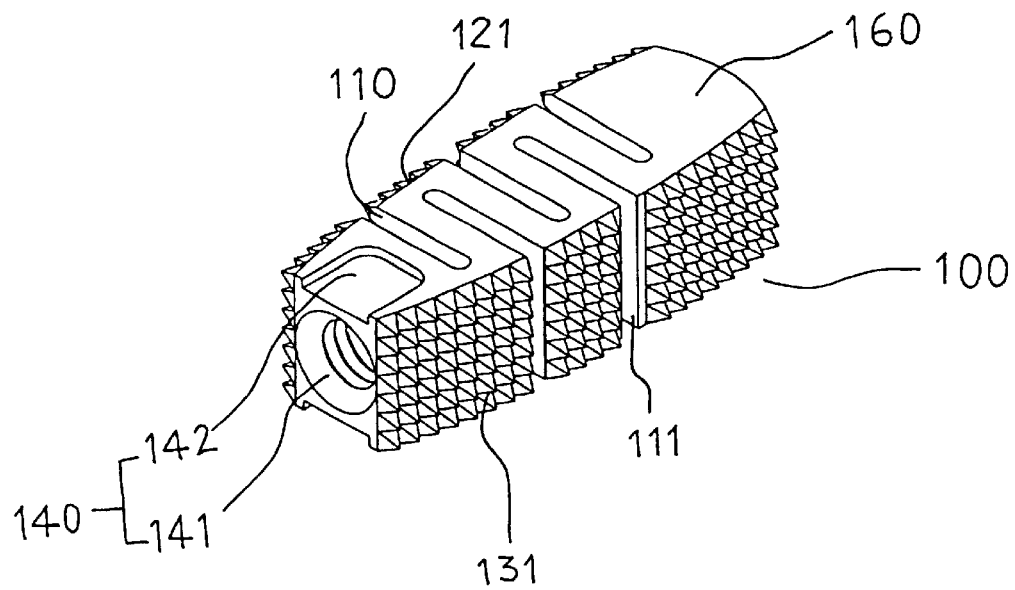
FIG. 1 shows a perspective view of a first preferred embodiment of the present invention.
Figure 2:
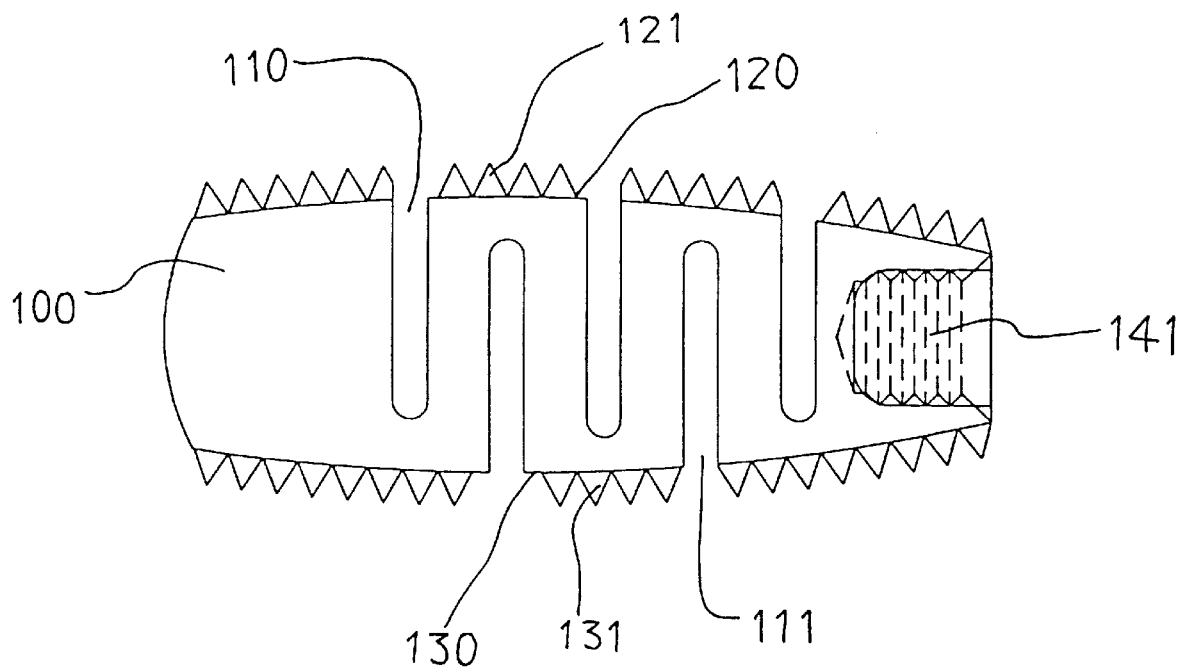
FIG. 2 shows a left side view of the first preferred embodiment of the present invention.
Figure 3:
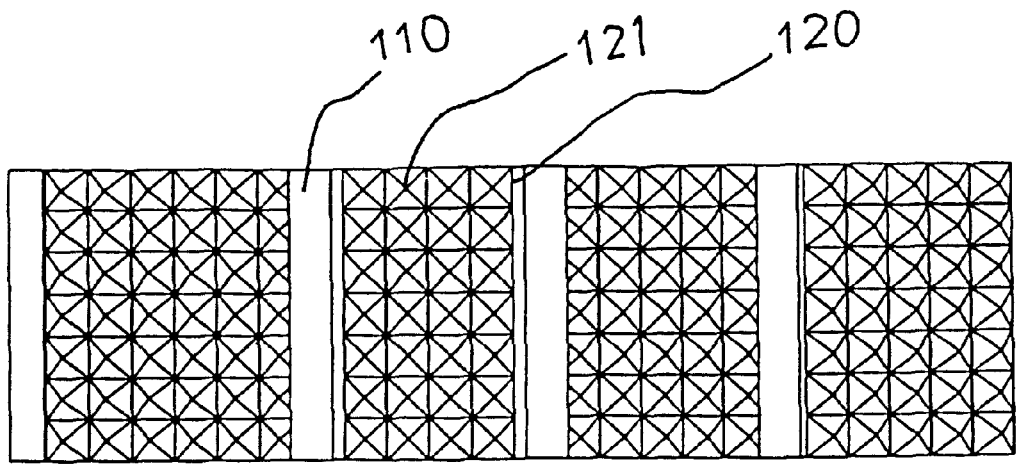
FIG. 3 shows a schematic view of the upper contact surface of the first preferred embodiment of the present invention.

As shown in FIGS. 1, 2 and 3, an elastic block body 100 embodied in the present invention is provided with a plurality of upward elastic slots 110 and a plurality of downward elastic slots 111. In fact, there are two upward elastic slots 111 and three downward elastic slots 110, which are arranged in an alternating manner of "downward upward downward upward downward." The elastic block body 100 is further provided on the upper contact surface 120 thereof with a plurality of protrusions 121, and on the lower contact surface 130 thereof with a plurality of protrusions 131. The elastic block body 100 is still provided with a rear surface 140 and a left surface 160. The rear surface 140 is provided with a tool hole 141, an upper tool slot 142, and a lower tool slot 143 (shown in FIG. 4). The tool hole 141 has threads on its surface.

Figure 4:
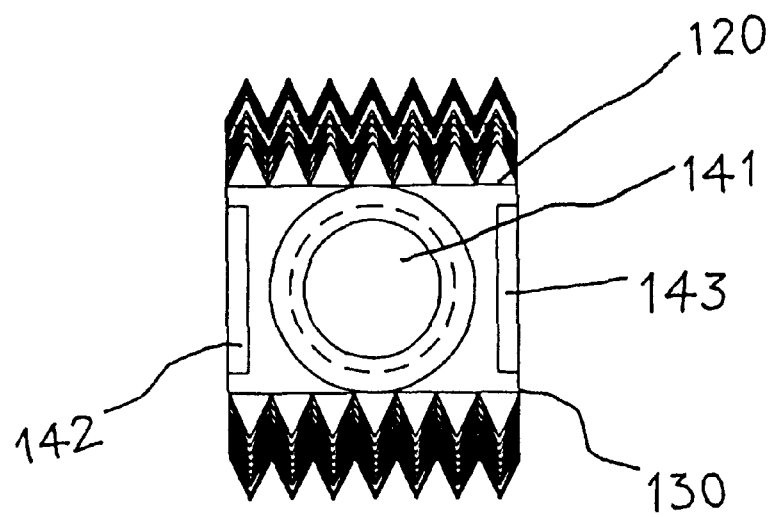
FIG. 4 shows a rear view of the first preferred embodiment of the present invention.

The upper contact surface 120 and the lower contact surface 130 of the present invention are of a convex construction, and respectively provided with a plurality of serrated protrusions which have increasing height from the rear (front) surface to the center of the body, as shown in FIG. 4.

Figure 5C:
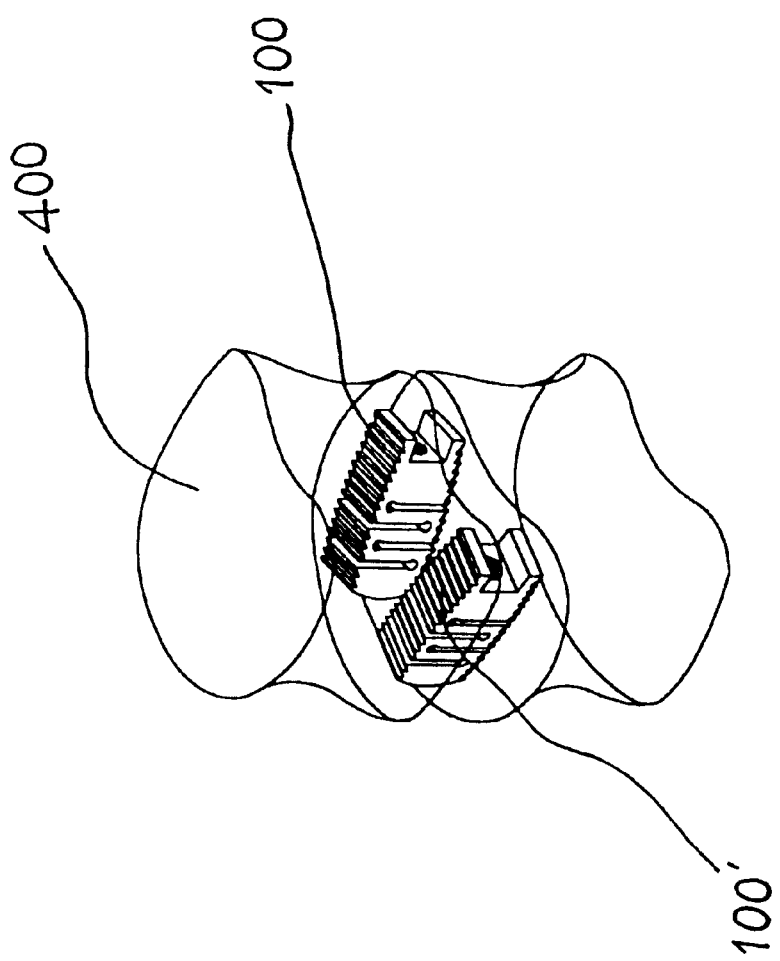

As shown in FIG. 5A, two adjoining vertebrae 400 and 450 are forced apart by a surgical tool 200, so as to enable the intervertebral fusion device 100 of the present invention to be implanted between the two vertebrae 400 and 450 by an implanting tool 300. The device 100 is implanted in such a manner that the right surface of the device 100 faces upward, and that the device 100 is turned by the tool 300 in the direction indicated by an arrow as shown in FIG. 5B, thereby forcing the upper contact surface and the lower contact surface of the device 100 to come in contact with the vertebrae 400 and 450. Now referring to FIG. 5C, another intervertebral fusion device 100' of the present invention is implanted in the manner described above. As shown in FIGS. 5A–5C, the intervertebral fusion devices 100 and 100' have stripe protrusions.

In view of the fact that both devices 100 and 100' of the present invention are provided with the elastic slots, these two devices 100 and 100' are capable of an automatic microadjustment in shape, so as to enable the two vertebrae 400 and 450 to remain in an intimate contact. As a result, the healing process is accelerated.

Figure 6:
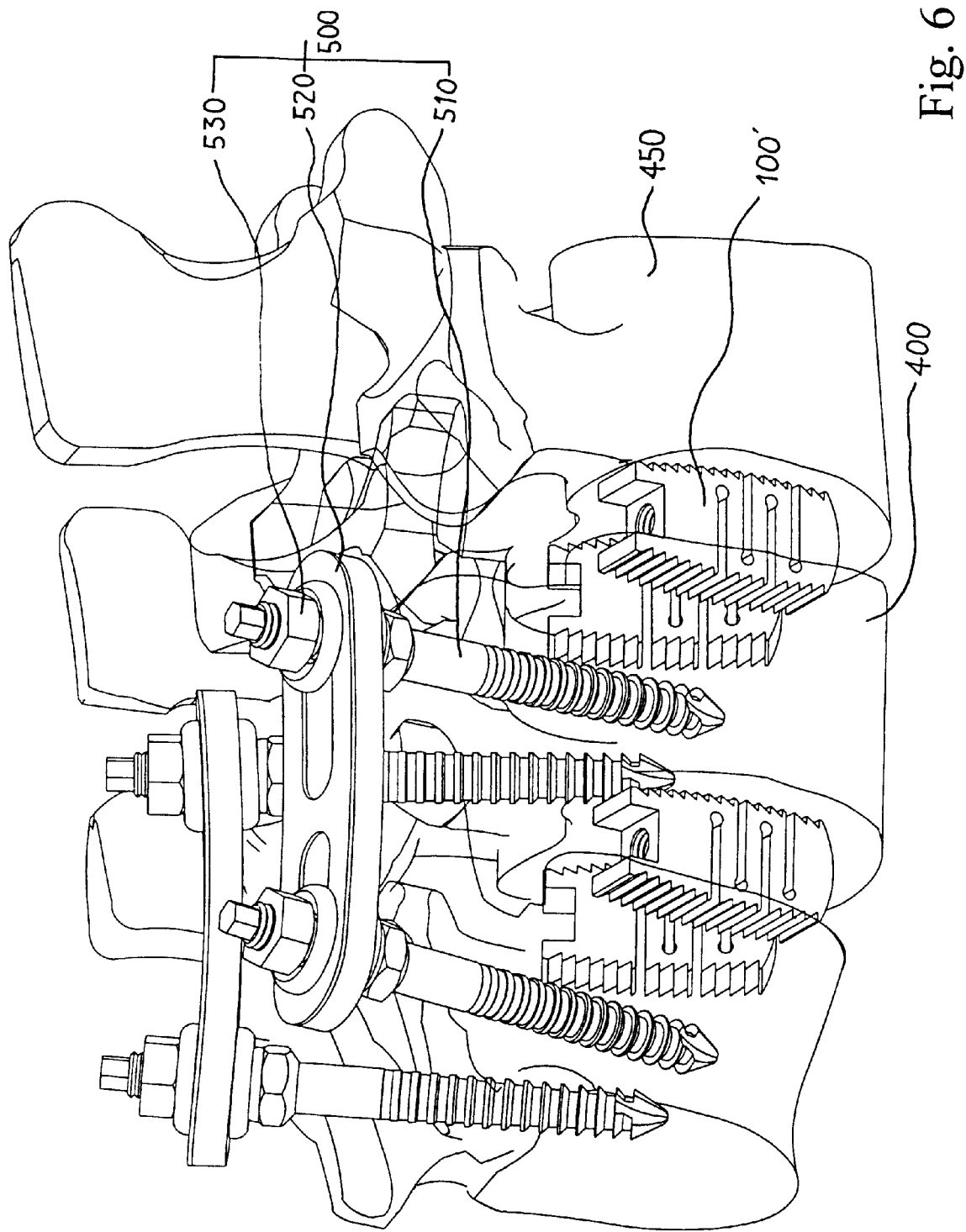
FIG. 6 shows a schematic view of the second preferred embodiment of the present invention at work in conjunction with an auxiliary device.

As shown in FIG. 6, the intervertebral fusion device 100' of the present invention is at work in conjunction with an auxiliary device 500 which comprises a plurality of bolts 510 and nuts 530, and a fastening plate 520.

What is claimed is:

1. An intervertebral fusion device formed of an elastic block body, wherein said elastic block body is provided in an upper contact surface thereof with a plurality of downward elastic slots substantially parallel to one another, and in a lower contact surface thereof with one or more upward elastic slots substantially parallel to said downward elastic slots, said upward elastic slots and said downward elastic slots being arranged in an alternating manner, said elastic block body further having a left surface and a right surface, which are substantially planar in construction, said upper contact surface and said lower contact surface being convex in construction.

2. The device as defined in claim 1, wherein said lower contact surface is provided with a plurality of upward elastic slots.

3. The device as defined in claim 2, wherein said upward elastic slots and said downward elastic slots are arranged in an alternating manner of "upward downward upward downward".

4. The device as defined in claim 1, wherein said left surface and said right surface are separated from each other by an interval, and wherein the convex surfaces of said upper contact surface and said lower contact surface have a maximum distance greater than the interval between said left surface and said right surface.

5. The device as defined in claim 4, wherein said upper contact surface and said lower contact surface are provided with a plurality of protrusions.

6. The device as defined in claim 5, wherein said upper contact surface and said lower contact surface are provided with a plurality of serrated protrusions or stripe protrusions.

7. The device as defined in claim 1, wherein said upper contact surface and said lower contact surface are provided with a plurality of protrusions.

8. The device as defined in claim 7, wherein said upper contact surface and said lower contact surface are provided with a plurality of serrated protrusions or stripe protrusions.

* * * * *